(12) United States Patent
Chandra (10) Patent No.: US 8,260,019 B2
(45) Date of Patent: Sep. 4, 2012

(54) METHODS AND APPARATUS FOR DATA COMMUNICATION ACROSS A SLIP RING

(75) Inventor: Naveen Stephan Chandra, Kenosha, WI (US)

(73) Assignee: General Electric Company, Schenectady, NY (US)

( * ) Notice: Subject to any disclaimer, the term of this patent is extended or adjusted under 35 U.S.C. 154(b) by 1188 days.

(21) Appl. No.: 11/893,731

(22) Filed: Aug. 17, 2007

(65) Prior Publication Data
US 2009/0046913 A1  Feb. 19, 2009

(51) Int. Cl.
*G06K 9/00* (2006.01)
(52) U.S. Cl. ............... 382/131; 382/232; 378/4; 378/8; 378/19; 378/21
(58) Field of Classification Search ............... 382/131, 382/232–253; 378/4, 8, 19, 21
See application file for complete search history.

(56) References Cited

U.S. PATENT DOCUMENTS

| | | | | |
|---|---|---|---|---|
| 4,458,267 A * | 7/1984 | Dolazza | | 378/98.7 |
| 4,815,118 A * | 3/1989 | Acharya et al. | | 378/19 |
| 5,018,174 A | 5/1991 | Collins | | |
| 5,208,581 A | 5/1993 | Collins | | |
| 5,579,357 A | 11/1996 | Harrison | | |
| 5,600,697 A | 2/1997 | Harrison | | |
| 5,828,273 A | 10/1998 | Harrison | | |
| 5,974,109 A * | 10/1999 | Hsieh | | 378/19 |
| 6,075,835 A * | 6/2000 | Acharya et al. | | 378/4 |
| 6,081,576 A | 6/2000 | Schanen et al. | | |
| 6,108,483 A | 8/2000 | Berkcan | | |
| 6,181,766 B1 | 1/2001 | Pearson, Jr. et al. | | |
| 6,198,791 B1 * | 3/2001 | He et al. | | 378/19 |
| 6,272,201 B1 | 8/2001 | Pan | | |
| 6,291,919 B1 | 9/2001 | Ganti et al. | | |
| 6,470,065 B1 * | 10/2002 | Lauther | | 378/4 |
| 6,535,572 B2 * | 3/2003 | Hsieh et al. | | 378/19 |
| 6,600,803 B2 * | 7/2003 | Bruder et al. | | 378/19 |
| 6,700,948 B2 | 3/2004 | Hoffman | | |
| 6,829,324 B2 * | 12/2004 | Mori et al. | | 378/4 |
| 7,006,592 B2 * | 2/2006 | Ali et al. | | 378/4 |
| 7,050,616 B2 | 5/2006 | Hsieh et al. | | |

(Continued)

FOREIGN PATENT DOCUMENTS

EP  0 429 261 A2  5/1991

(Continued)

*Primary Examiner* — Matthew Bella
*Assistant Examiner* — Eric Rush
(74) *Attorney, Agent, or Firm* — The Small Patent Law Group; Dean D. Small (57) ABSTRACT

A method for reducing bandwidth required for transmission of data in a device having two portions rotating with respect to one another. The first portion includes a data acquisition system (DAS) having a charge-to-digital converter and a digital signal processor (DSP) configured to receive and compress digital data from the charge-to-digital processor. The second portion includes a computer configured to receive data from the DAS. The DAS and computer are communicatively coupled via a slip ring having a finite transmission bandwidth. The computer is configured to reconstruct and display an image using compressed data. The method includes using the DAS to compress scan data to a predetermined number of mantissa bits and a predetermined number of exponent bits, transmitting the compressed data from the first portion to the second portion across the slip ring, and using the transmitted compressed data to reconstruct and display an image of an object.

20 Claims, 8 Drawing Sheets

U.S. PATENT DOCUMENTS

| | | |
|---|---|---|
| 7,068,206 B2 | 6/2006 | Augusto et al. |
| 7,164,379 B1 | 1/2007 | Rao |
| 7,327,866 B2 * | 2/2008 | Bae et al. ............... 382/131 |
| 7,476,026 B2 * | 1/2009 | Braunstein ............ 378/207 |
| 2006/0050839 A1 * | 3/2006 | Balan et al. ............ 378/4 |

FOREIGN PATENT DOCUMENTS

| | | |
|---|---|---|
| EP | 0 543 623 B1 | 8/1998 |
| EP | 1 351 194 A1 | 10/2003 |

* cited by examiner

METHODS AND APPARATUS FOR DATA COMMUNICATION ACROSS A SLIP RING

BACKGROUND OF THE INVENTION

This invention relates generally to an imaging apparatus, and more particularly, to a diagnostic imaging apparatus having a rotating portion and a stationary portion with a slip ring between the rotation portion and the stationary portion across which data is transmitted.

In some computed tomography (CT) imaging systems, an x-ray source projects a fan-shaped beam that is collimated to lie within an X-Y plane of a Cartesian coordinate system and generally referred to as an "imaging plane." The x-ray beam passes through an object being imaged, such as a patient. The beam, after being attenuated by the object, impinges upon an array of radiation detectors. The intensity of the attenuated beam radiation received at the detector array is dependent upon the attenuation of an x-ray beam by the object. Each detector element of the array produces a separate electrical signal that is a measurement of the beam attenuation at the detector location. The attenuation measurements from all the detectors are acquired separately to produce a transmission profile.

In third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view." A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units," which are used to control the brightness of a corresponding pixel on a cathode ray tube display or film.

To reduce the total scan time, a "helical" scan may be performed. To perform a "helical" scan, the patient is moved while the data for the prescribed number of slices is acquired. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered back projection process, the data is weighted according to a helical weighing factor, which is a function of both the gantry angle and detector angle. The helical weighting algorithms also scale the data according to a scaling factor, which is a function of the distance between the x-ray source and the reconstruction plane. The weighted and scaled data is then processed to generate CT numbers and to construct an image that corresponds to a two dimensional slice taken through the object. Alternatively, interpolation can be performed on the collected projection data to produce a set of projections corresponding to the reconstruction plane. Filtered backprojection is then used to construct an image that corresponds to a two-dimensional slice taken through the object.

At least one known CT imaging system during normal scanning sends imaging data collected by a detector array across a slip ring having a shoe and a copper ring mechanism. A receiver of the imaging data checks the data and, if the data is correct, sends an acknowledgement to a transmitter that the correct imaging data was received. However, as scan speeds are increased and additional data is collected in the detector array, data must be transmitted over the slip ring at a faster rate. As a result, there may be insufficient bandwidth to provide a communication path back from the receiver of the imaging data to the transmitter or even to transmit the data itself across the slip ring. Thus, scanning speed is limited by the bandwidth of data transmission across the slip ring.

BRIEF DESCRIPTION OF THE INVENTION

In one aspect, the present invention provides a method for reducing bandwidth required for transmission of data in a device having two portions rotating with respect to one another is provided. The first portion includes a data acquisition system (DAS) having a charge-to-digital converter and a digital signal processor (DSP) configured to receive and compress digital data from the charge-to-digital processor. The second portion includes a computer or processor configured to receive data from the DAS. The DAS and computer or processor are communicatively coupled via a slip ring having a finite transmission bandwidth, and the computer or processor is configured to reconstruct and display an image using compressed data. The method includes using the DAS to compress scan data to a predetermined number of mantissa bits and a predetermined number of exponent bits, transmitting the compressed data from the first portion to the second portion across the slip ring, and using the transmitted compressed data to reconstruct and display an image of an object.

In another embodiment, an imaging apparatus having a first portion and a second portion rotating with respect to one another is provided. The first portion includes a radiation source, a detector array configured to detect radiation from the radiation source passing through an object and to produce an electrical charge indicative of the radiation detected, and a data acquisition system (DAS). The DAS includes a charge-to-digital converter coupled to the detector array and a digital signal processor (DSP) configured to receive and compress digital scan data from the charge-to-digital processor to a predetermined number of mantissa bits and a predetermined number of exponent bits. The second portion includes a processor configured to receive compressed data from the DAS. The DAS and processor are communicatively coupled via a slip ring having a finite transmission bandwidth. The processor is configured to reconstruct an image using the compressed data. The second portion also includes a display coupled to the processor to display the image produced by the processor.

In yet another embodiment, a method for scanning a patient using a medical CT imaging system having two portions rotating with respect to one another is provided. The first portion of the CT imaging system includes a x-ray tube and a detector on a rotating gantry, a data acquisition system (DAS) having a charge-to-digital converter coupled to a substrate of the detector, and a digital signal processor (DSP) configured to receive and compress digital scan data from the charge-to-digital processor. The second portion of the CT imaging system includes a processor configured to receive compressed data from the DAS. The DAS and processor are communicatively coupled via a slip ring having a finite transmission bandwidth, and the processor is configured to reconstruct and display an image using the compressed data. The method includes operating the CT imaging system to rotate the gantry, x-ray tube, and detector to scan a region of interest of the patient and develop charges on the detector, converting the charges on the substrate of the detector to digital count scan data using the charge-to-digital converter, and using the DAS to compress the digital count scan data to a predetermined number of mantissa bits and a predetermined number of exponent bits. The method further includes transmitting the compressed data from the first portion to the second portion across the slip ring and using the transmitted compressed data to reconstruct and display an image of the region of interest of the patient.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

DETAILED DESCRIPTION OF THE INVENTION

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 1:
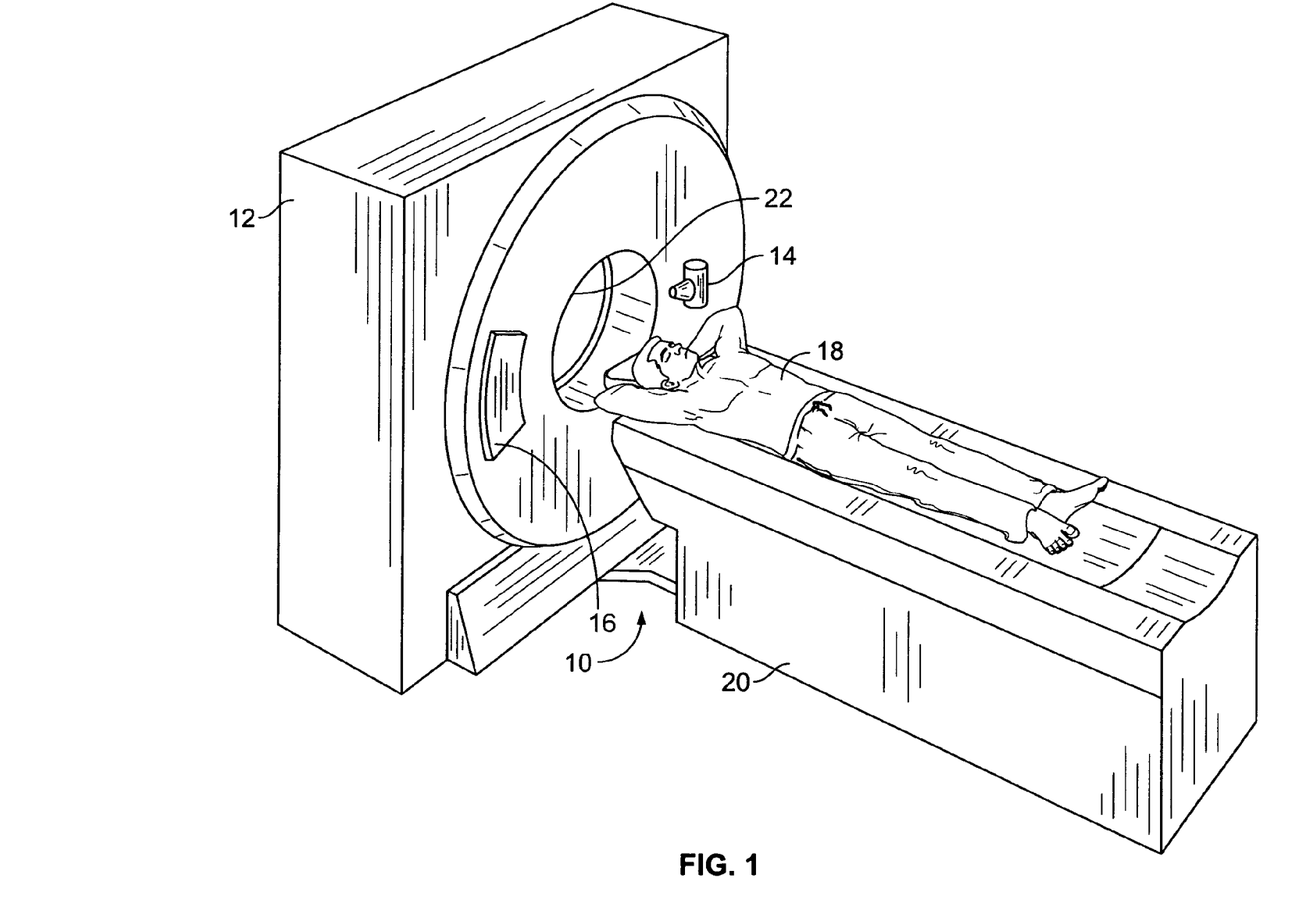
FIG. 1 is a pictorial view of a CT imaging system constructed in accordance with various embodiments of the invention.

Referring now specifically to FIG. 1, a computed tomography (CT) imaging system 10 is shown as including a gantry 12 representative of a "third generation" CT scanner. Gantry 12 has a radiation source such as x-ray source 14 that projects a beam of x-rays toward a detector array 16 on the opposite side of gantry 12. Detector array 16 is formed by a plurality of detector modules that together sense the projected x-rays that pass through an object 18 such as, but not limited to, a medical patient 18. Each detector module produces an electrical signal that represents the intensity of an impinging x-ray beam and hence the attenuation of the beam as it passes through patient 18.

During a scan to acquire x-ray projection data, gantry 12 and the components mounted thereon rotate about a center of rotation. A motorized table 20 positions patient 18 relative to gantry 12. Particularly, table 20 moves portions of patient 18 through a gantry opening 22 during a scan.

Figure 2:
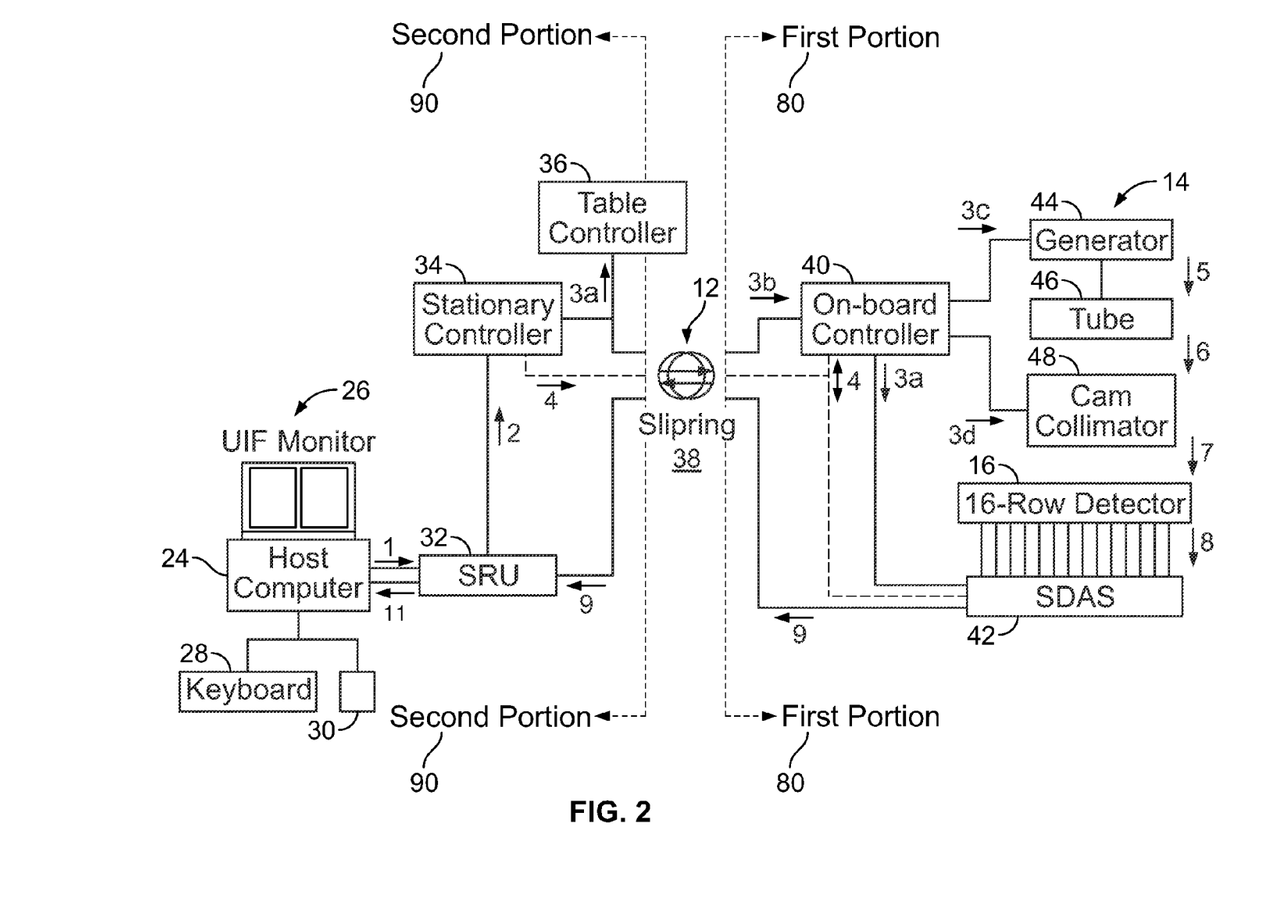
FIG. 2 is a block schematic diagram of the system illustrated in FIG. 1.

FIG. 2 is a block schematic diagram of the system illustrated in FIG. 1. As shown in FIG. 2, system 10 includes a host computer 24 coupled to a monitor (user interface) 26 for displaying images and messages to an operator. Computer 24 also is coupled to a keyboard 28 and an input device 30 such as a mouse 30 to enable the operator to input information and commands to computer 24. Computer 24 is coupled to a scan and reconstruction control unit (SRU) 32. SRU 32 also includes image generation controls. In one specific embodiment, SRU 32 includes a SGI PCI-based central processing unit that operates on an IRIX operating system. SRU 32 also includes an interface processor for interfacing with the data acquisition system (described below), and a scan data correction digital signal processing board for performing preprocessing, which is known in the art. SRU 32 further includes an image generator for filtered backprojection and postprocessing operations, as is known in the art.

A stationary controller 34 is connected to SRU 32, and stationary controller 34 is coupled to a table controller 36. Stationary controller 34 also is connected, through a slip ring 38, to an on-board controller 40 and a scalable data acquisition system (SDAS) 42 or a global data acquisition system (GDAS), which is used in some embodiments. Slip ring 38 enables contactless transmission of signals across the slip ring boundary and supports the necessary bandwidth for transmission of data and commands across the boundary. SDAS 42 or GDAS samples and acquires the data from detector 16 and converts the sampled analog signals to digital signals. SDAS 42, in one specific embodiment, includes forty eight interchangeable converter cards to support four row data acquisition. For two row data acquisition, twenty four cards could be used. In one specific embodiment, there are sixty four input channels per converter card and 1408 Hz sampling can be performed. SDAS 42 or GDAS also includes a frontend pre-amplifier for amplifying the signals. In one embodiment, SDAS 42 is not scalable and is sometimes referred to herein as data acquisition system (DAS) 42. Embodiments of the present invention may be used with or employ a DAS, an SDAS, or a GDAS, so the term "DAS" as used herein includes DAS, SDAS, and GDAS within its generic scope.

On-board controller 40 controls operation of x-ray source 14 and operation of DAS 42. X-ray source 14 includes a high voltage generator 44 coupled to an x-ray tube 46. Tube 46 may, for example, a tube known in the art such as the Gemini-1 tube currently utilized in at least some CT systems commercially available from General Electric Company, Milwaukee, Wis., 53201. Beams projected by X-ray tube 46 pass through a prepatient cam collimator 48 and impinge upon detector 16 (illustrated as a 16 row detector). Cam collimator 48 also is controlled by on-board controller 40. Outputs from detector 16 are supplied to DAS 42.

In FIG. 2, data flow is illustrated by bold lines, control flow is illustrated by normal lines, and real-time control flow is illustrated by dashed lines. The numeric identifiers associated with the flows are set forth below.

1: scan and reconstruction prescription from operator
2: scan prescription to "master" controller
3: scan parameters distributed
3a: table position
3b: rotating parameters
3c: kV and mA selections
3d: x-ray beam collimation and filter selections
3e: detector slice thickness and SDAS or GDAS gain selections
4: real-time control signals during scanning
5: high voltage
6: un-collimated x-ray beam
7: collimated x-ray beam
8: analog scan data
9: digital scan data
11: patient images Rotation of gantry 12 and the operation of x-ray source 14 are governed by controller 34. On-board controller 40, under the control of stationary controller 34, provides power and timing signals to x-ray source 14. DAS 42 samples analog data from detector 16 and converts the data to digital signals for subsequent processing. SRU 32 receives sampled and digitized x-ray data from DAS 42 and performs high speed image reconstruction. The reconstructed image is applied as an input to computer 24 that stores the image in a mass storage device.

Computer 24 also receives commands and scanning parameters from an operator via keyboard 28 and mouse 30. Monitor 26 allows the operator to observe the reconstructed image and other data from computer 24. The operator supplied commands and parameters are used by computer 24 to provide control signals and information. In addition, controller 36 controls motorized table 20 to position patient 18 (shown in FIG. 1).

Generally, the above described CT system is operable to collect one, two or more slices data. Axial and helical scans can be performed with the system, and cross section images of a scanned object can be processed, reconstructed, displayed and/or archived. Scalable axial image reconstruction and display refers, for example, to selectability of the image thickness, number of slices, and number of images to be displayed. Further, the system is not limited to practice with any one particular image reconstruction algorithm, and it is contemplated that many different reconstruction algorithms can be utilized. Exemplary algorithms are set forth in U.S. Pat. Nos. 5,469,487, 5,513,236, 5,541,970, 5,559,847, 5,606, 585, and 5,828,719, all of which are assigned to the present assignee.

In one embodiment, computer 24 includes a device (not shown), for example, a floppy disk drive or CD-ROM drive, for reading instructions and/or data from a computer-readable medium (not shown), such as a floppy disk or CD-ROM. In another embodiment, computer 24 executes instructions stored in firmware (not shown). Computer 24 is programmed to perform functions described herein, but other programmable circuits can be likewise programmed. For example, in one embodiment, DAS 42 performs functions described herein. Accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Additionally, although described in a medical setting, it is contemplated that the benefits of the invention accrue to all CT systems including industrial CT systems such as, for example, but not limited to, a baggage scanning CT system typically used in a transportation center such as, for example, but not limited to, an airport or a rail station. Furthermore, the benefits of the present invention accrue not only to CT systems, but to all high-bandwidth systems (imaging or otherwise) having to transmit data across a rotating slip ring.

Figure 3:
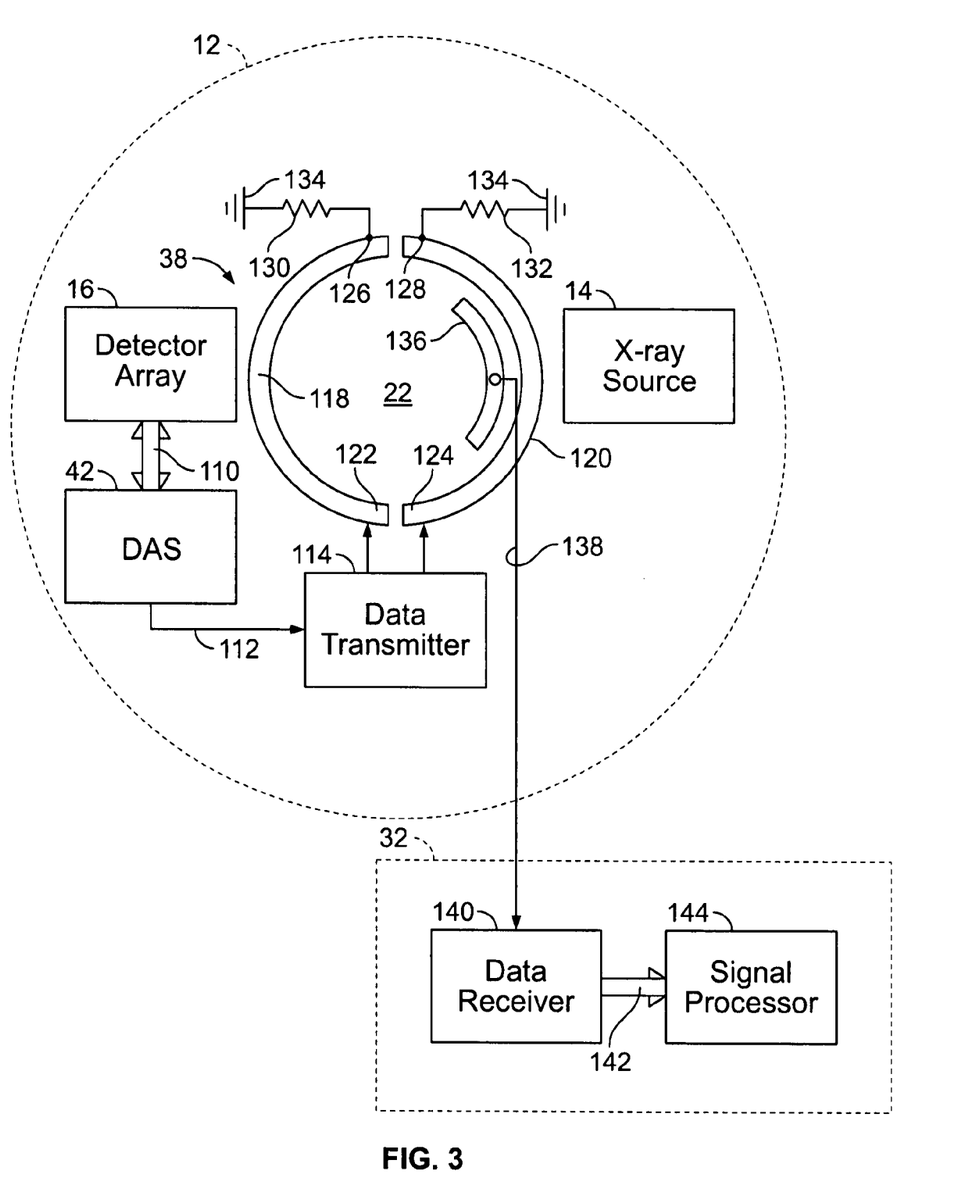
FIG. 3 is a simplified, figurative schematic block diagram of the gantry of the system illustrated in FIGS. 1 and 2.

Referring now to FIG. 3, which is a simplified, figurative schematic block diagram of gantry 12. The signals from detector array 16 are provided through lines 110 to data acquisition system DAS 42, which converts each signal from an analog signal format (e.g., charges stored in a semiconductor array below scintillator crystals in detector array 16) into digital data (also called "scan data" herein), typically, two bytes having 16 bits. The digital data is provided on lines 112 to a data transmitter 114 disposed on gantry 12. Data transmitter 114 digitally encodes the scan data with a radio frequency (RF) pulse pattern, and the RF encoded signal is presented to an electromagnetic coupler, such as an RF slip ring 38 similar to the type disclosed in U.S. Pat. No. 5,530,424 to Harrison et al, which is assigned to the assignee of this application.

The slip ring configuration includes one or more transmission lines disposed on the rotating side of the interface one coupler segment mounted on the stationary side. Depending on the distance between the stationary coupler and the rotating transmission line, a number of transmission line segments may be required to ensure that the coupler is always in spatial proximity to at least one of the segments to receive the electromagnetic signal. In that case, each segment has a length that is a fractional portion of the arc length of the gantry's rotational path. The segments are cascaded, end-to-end around the gantry's rotational axis, typically along the circumference of opening 22 such that the aggregate length provides a substantially 360 degree arc, i.e. a full rotation of the gantry.

Two transmission line segments 118, 120 are used and are mounted in a manner to provide adjacent positioning of first ends 122, 124 and second ends 126, 128 of transmission lines 118, 120, respectively. Contiguous placement of the ends of each of the transmission lines provides substantial continuity of the electromagnetic coupling along the full rotational path of the gantry.

Data transmitter 114 provides the encoded data to first ends 122, 124 of each of the transmission lines 118, 120. Second ends 126, 128 of each transmission line are connected through terminal impedances 130, 132 to signal ground 134. A coupler element 136 is positioned on the stationery frame in a manner to ensure physical proximity of the coupler to one and both of the transmission lines 118, 120 during gantry rotation. The encoded data is electromagnetically coupled through to coupler 136, for example, as described in U.S. Pat. No. 5,530,424. However, in other embodiments of the present invention, electrical signals are transmitted across slip ring 38 using conductive brushes (not shown in the Figures).

On the stationery frame side, the coupled data signal is provided on a line 138 to SRU 32. The encoded data is received at a data signal receiver 140. Signal receiver 140 decodes the serial data and provides the decoded data through lines 142 to a signal processor 144. Signal processor 144 includes signal memory (not shown) for storing the program algorithms that govern the CT processing of the received data in response to operator commands. Signal processor 144 collates the decoded imaging data sets into a composite view associated with the particular angular position of the gantry.

Figure 4:
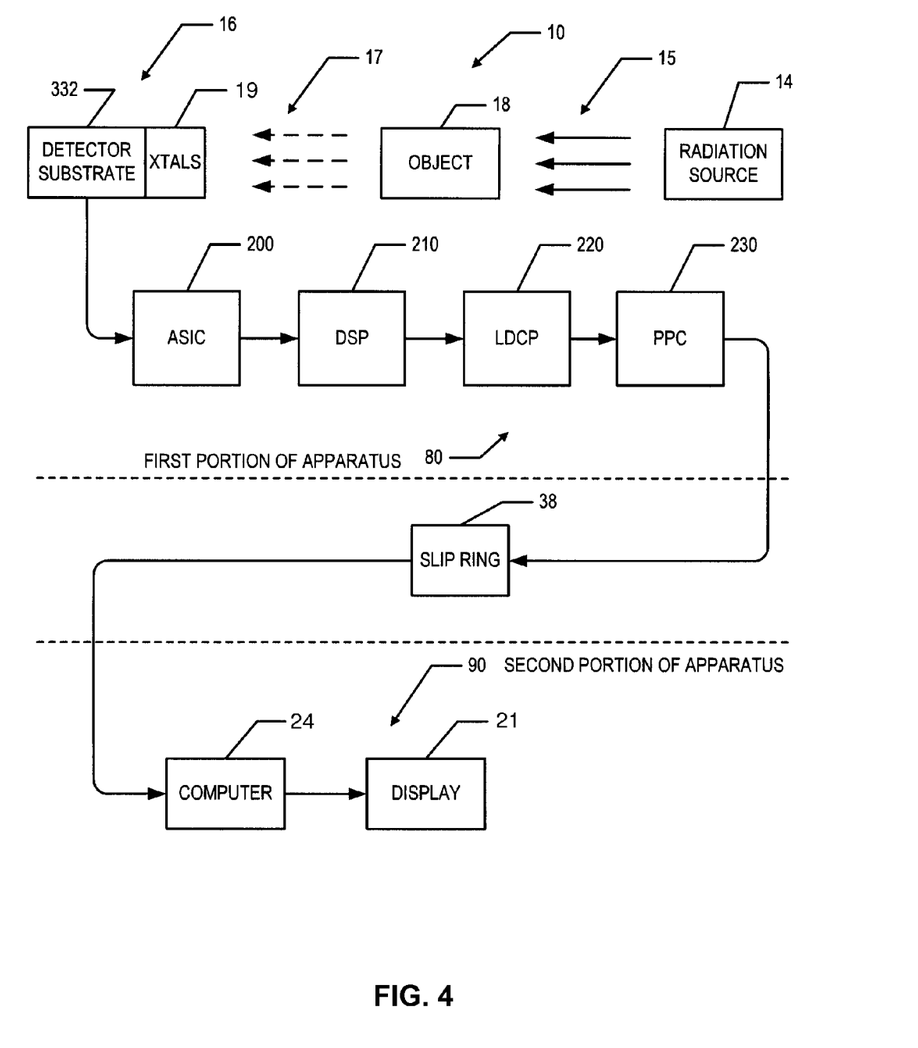
FIG. 4 is a block diagram of a data path through a data acquisition system in one embodiment of the present invention.

FIG. 4 is a block diagram of a data path through a DAS 42 in one embodiment of the present invention. Imaging system 10 comprises a first portion 80 and a second portion 90 configured to rotate with respect to one another. In a CT imaging apparatus 10, first portion 80 is often referred to as the rotating portion or side and second portion 90 is often referred to as the stationary portion or side. In first portion 80, radiation source 14 emits radiation 15 that passes through an object 18. Object 18 is on table 20, neither of which is considered part of first portion 80. The attenuated radiation 17 that passes through object 18 strikes detector 16, which, in one embodiment, comprises scintillator crystals 19 that convert radiation 17 to visible light that is detected by and transformed into electrical charges by detector elements or sensors 110 in the detector substrate. An application specific integrated circuit (ASIC) 200 includes at least one charge-to-digital converter configured to convert the charge on detector elements 110 into digital counts that comprise the scan data. For example, ASIC 200 is an ASIC described in U.S. Patent Nos. 6,366,231, 7,095,354, and/or 7,164,319, all assigned to the assignee of this application.

Figure 5:
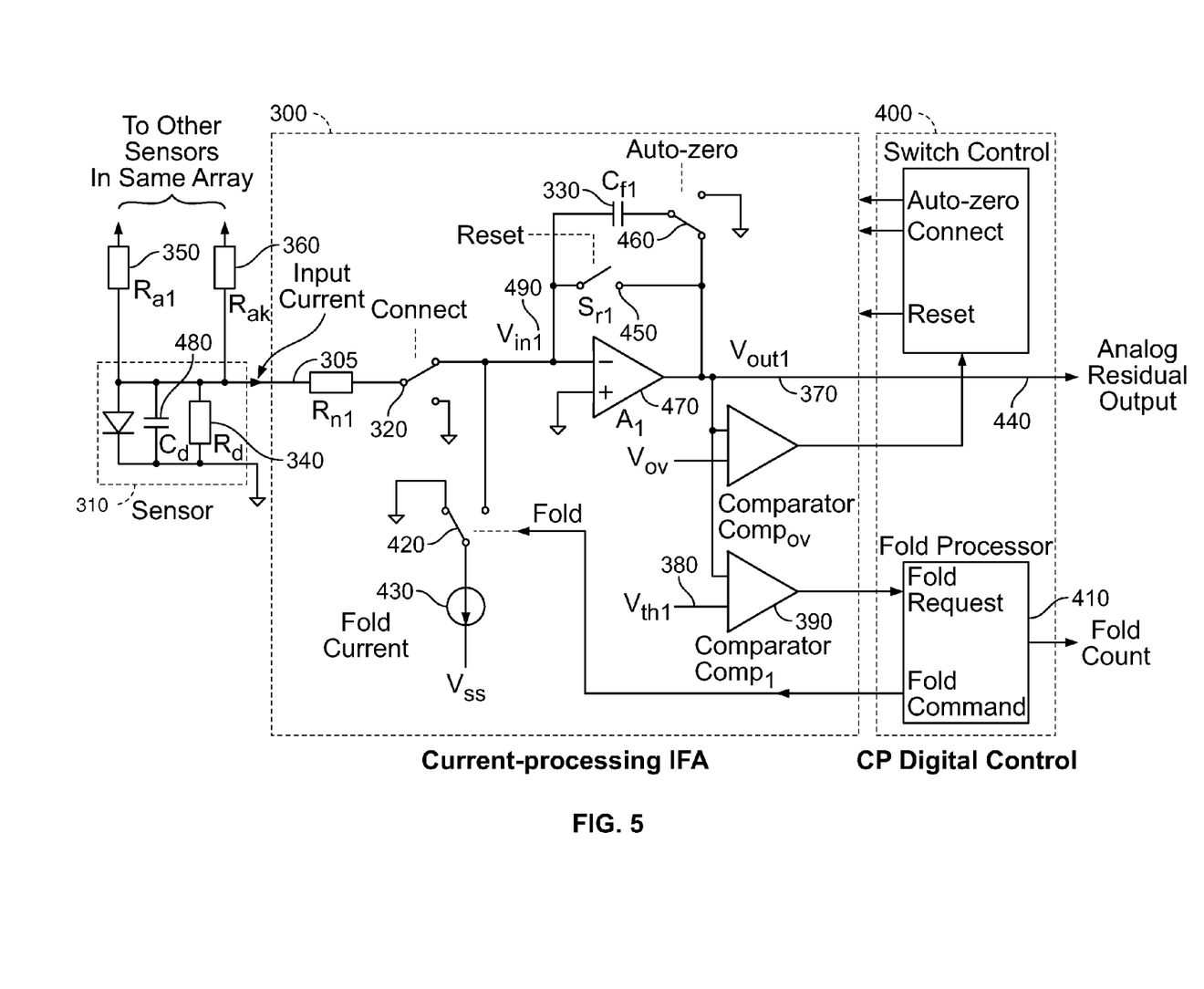
FIG. 5 is a block schematic diagram of a current processing integrate and fold amplifier (CPIFA) used to convert a charge on a detector substrate of the detector in the CT imaging apparatus of FIG. 1 to digital scan data.

A current processing integrate and fold amplifier stage (CPIFA) 300 of ASIC 200 is shown in block schematic form in FIG. 5. CPIFA stage is shown with switch positions set for normal integration. Current flows from sensor 310 through switch $S_d$ 320 into integration (feedback) capacitor $C_{f1}$ 330. Sensor 310 is typically one of an array of sensors on a common integrated circuit substrate, such as an X-ray detection element of detector array 16. Resistor $R_d$ 340 represents the sensor self-leakage resistance, and resistors $R_{a1}$ 350 through $R_{ak}$ 360 represent the between-sensor leakage resistances to k other sensors. The resistance values are usually very high, but the effect of this resistance often cannot be ignored. A charge accumulates on feedback capacitor $C_{f1}$ 330 and stage-1 output voltage $V_{out1}$ 370 becomes proportionally more negative. With positive current, $V_{out1}$ 370 eventually becomes more negative than threshold voltage $V_{th1}$ 380 so that comparator 390 trips and requests a "fold" from fold processor 410 in digital control block 400. When appropriate, fold processor 410 responds with an accurately timed fold pulse that switches fold switch 420 thus removing fold current $I_{fold1}$ 430 from integration capacitor 330 for the pulse duration. (A "fold" is a specific amount of charge that is removed from the amplifier which leads to a defined change in the voltage on the output of the amplifier. A "fold pulse" is a pulse lasting an amount of time required for a current source to be turned on to remove a required amount of charge.) Over an integration period, multiple fold requests and folds may occur and the number of folds is counted for that integration period. At the end of the integration period, after all folding is completed, a residual charge remains on integration capacitor 330 and the charge is proportionally represented by $V_{out1}$ 370 at the analog residual output 440. This voltage can be processed by the voltage-processing IFA stage 400 of FIG. 5 (or by conventional analog-to-digital conversion means) to extract more digital resolution of the total integrated charge.

At the end of each integration period, after the analog residual output 440 has been sampled by a following stage (not shown) or by an A/D converter (not shown), the stage-1 IFA can be reset so that the analog residual value starts at zero for each integration period. This is the "resetting mode" of CPIFA operation. Alternatively, this reset can be eliminated, but then the stage-1 fold count and the change in stage-1 analog residual together indicate the total integrated charge. This is the "no-resetting" mode of CPIFA operation.

Referring further to FIG. 5, in the resetting mode, before each integration period begins, reset switch $S_{r1}$ 450 is closed and auto-zero switch $S_{az1}$ 460 is connected to ground. This eliminates the prior residual charge from integration capacitor $C_{f1}$ 330 and onto the parasitic sensor and interconnection capacitance $C_d$ 480. This makes the stage-1 analog residual value zero when the total input charge is zero.

In the no-resetting mode, current is continually integrated. Also, reset switch 450 is not closed and auto-zero switch 460 is not connected to ground. At this stage the input potential drop for the amplifier 470 is equal to $V_{in1}$ 490. This has the advantage that inherent noise from amplifier 470 is not sampled onto $C_{f1}$ 330 and $C_d$ 480 as is done at the end of the reset period in the resetting mode of operation.

Referring again to FIG. 4, ASIC 200 produces a high-resolution digital data output. DAS 42 then provides additional data formatting to compile count values and to linearize data from ASIC 200. This formatted output is further processed by a digital signal processor (DSP) 210, which scales the high-resolution input data. This scaling determines the least significant bit (LSB) of DAS 42 and also results in the gain of sub-LSB resolution in DAS 42. The output of DSP 210 is applied to a lossy data compression processor (LDCP) 220 that results in some loss of resolution in DAS 42. In some embodiments of the present invention, further compression is applied by a post-processing compressor (PPC) 230 in DAS 42. The output of DAS 42 is transmitted from apparatus first portion 80 to apparatus second portion 90 across slip ring 38, where computer 24 uses the compressed data received to generate an image of object 18 on display 21.

As used herein, the term DSP (as in DSP 210) is not intended to be limited only to DSPs. Instead, recitations of the term DSP are also intended to include literally within their scope appropriately programmed field programmable gate arrays (FPGAs) and custom digital integrated circuits. Such "appropriately programmed" FPGAs and "custom" digital integrated circuits are configured so as to perform essentially the same functions recited for the DSP.

Data from ASIC 200 does not necessarily have the same LSB resolution as that of the overall output of DAS 42. For simplicity, ease of implementation, and/or cost reasons, data generated by DAS 42 can be further reduced by applying scaling to the ASIC data and by rounding in the data path prior to data transmission. The overall linearity of DAS 42 can be different from the linearity of ASIC 200. In some embodiments of the present invention, this rounding is performed to convert the linearized ASIC data from a floating point number to an integer. After the data has been scaled and rounded, the data undergoes another formatting step in LDCP 220, which in some embodiments of the present invention, packs data into a 16 bit format, with a 14 bit mantissa and a 2 bit exponent. In other embodiments, data is packed into other formats, one example of which is a 16 bit format with a 12 bit mantissa and a 4 bit exponent. This packing results in a lossy compression, which truncates bits depending upon signal level. The lossiness of the compression does not cause problems as long as the increased quantum noise at higher signal levels can be represented by at least 2 bits in LDCP 220. Various ad hoc static and/or dynamic scaling methods are used in LDCP 220 depending upon noise, linearity, and dynamic range requirements of any particular embodiment.

CT imaging systems, such as imaging system 10, have unique physical properties that allow for geometric, spatial, and temporal compression methods to be used which, although lossy in principle, result in reconstruction of images with equivalent image quality.

To minimize, or at least conserve, data transmission bandwidth, DAS output data can be compressed into a lossy or preferably lossless format and transmitted across slip ring 38.

The conservation of data transmission bandwidth benefits a CT imaging system 10 in that a reduction in DAS 42 specification requirements, slip ring 38 requirements, disk write speed requirements, and/or data storage space required to store scan information can be achieved. Either more data (e.g., more image slices and/or channels) can be used or a reduction in component performance requirements (and thus, cost) can be achieved.

To make the proper system tradeoffs, the proper type or types of lossy compression performed is selected in some embodiments of the present invention. An appropriate lossy compression method avoids problems relating to noise normality, linearity, signal dynamic range, and/or image quality.

In some embodiments of the present invention, compression is applied to raw data in DSP 210, before it is further compressed by LDCP 220. In some embodiments of the present invention, compression is applied to raw data in DSP 210 irrespective of whether any further data compressed is applied by LDCP 220. Also, in some embodiments of the present invention, PPC 230 is present and is configured to further compress the data transmitted across slip ring 38.

Figure 6:
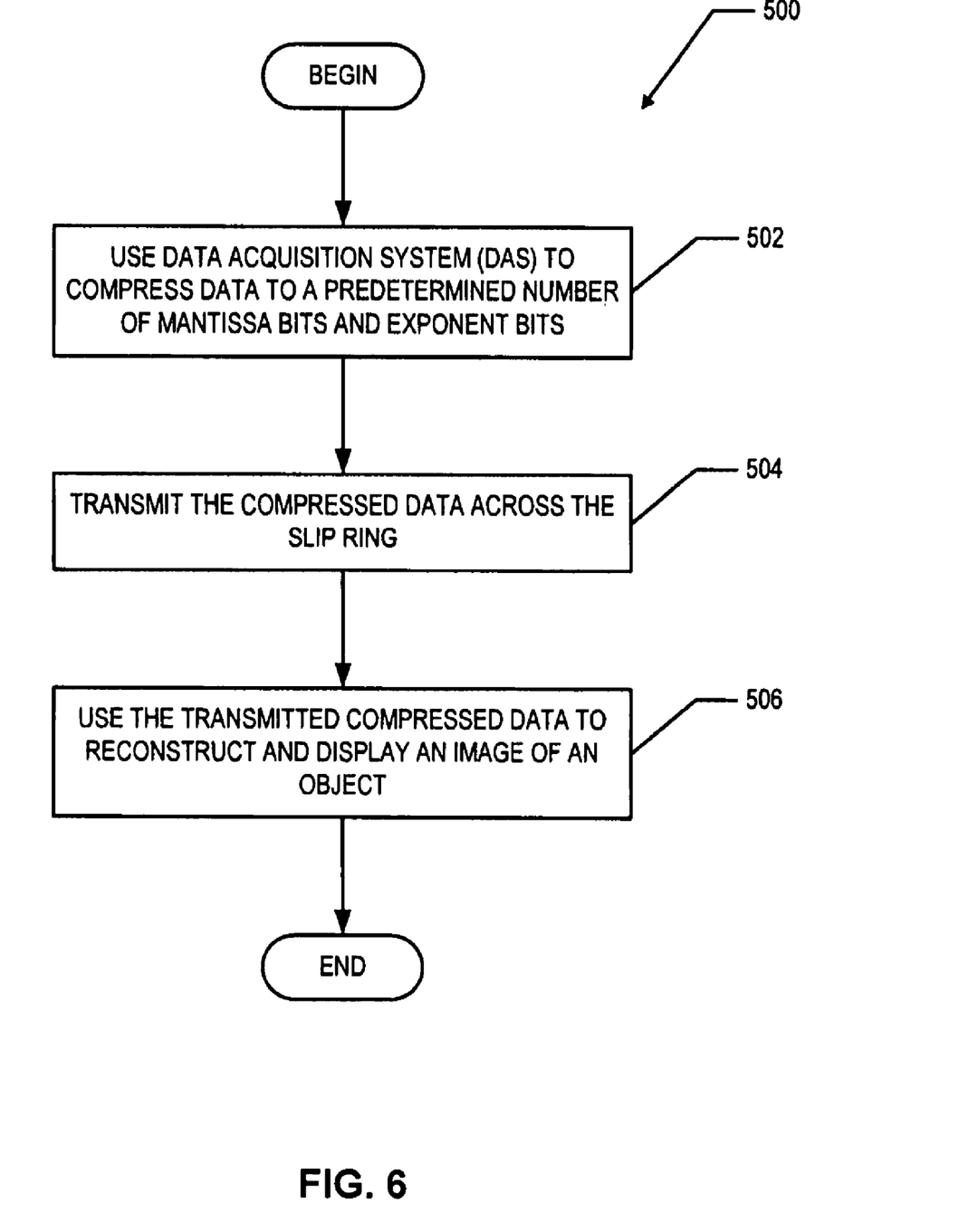
FIG. 6 is a flow chart of a method according to an embodiment of the present invention.

FIG. 6 is a flow chart 500 representing an embodiment of the present invention. In the represented embodiment, the bandwidth required to transmit data from a first portion of a device to a second portion of the device, wherein the first portion and the second, portion are rotating with respect to one another, is reduced. The method includes, at 502, using DAS 42 to compress data to a predetermined number of mantissa bits and a predetermined number of exponent bits. Next, at 504, the data compressed at 502 is transmitted from the first portion of the apparatus to the second portion of the apparatus across slip ring 38. Next, at 506, the compressed data transmitted at 504 is used by computer 24 to reconstruct and display an image of an. object 18.

Figure 7:
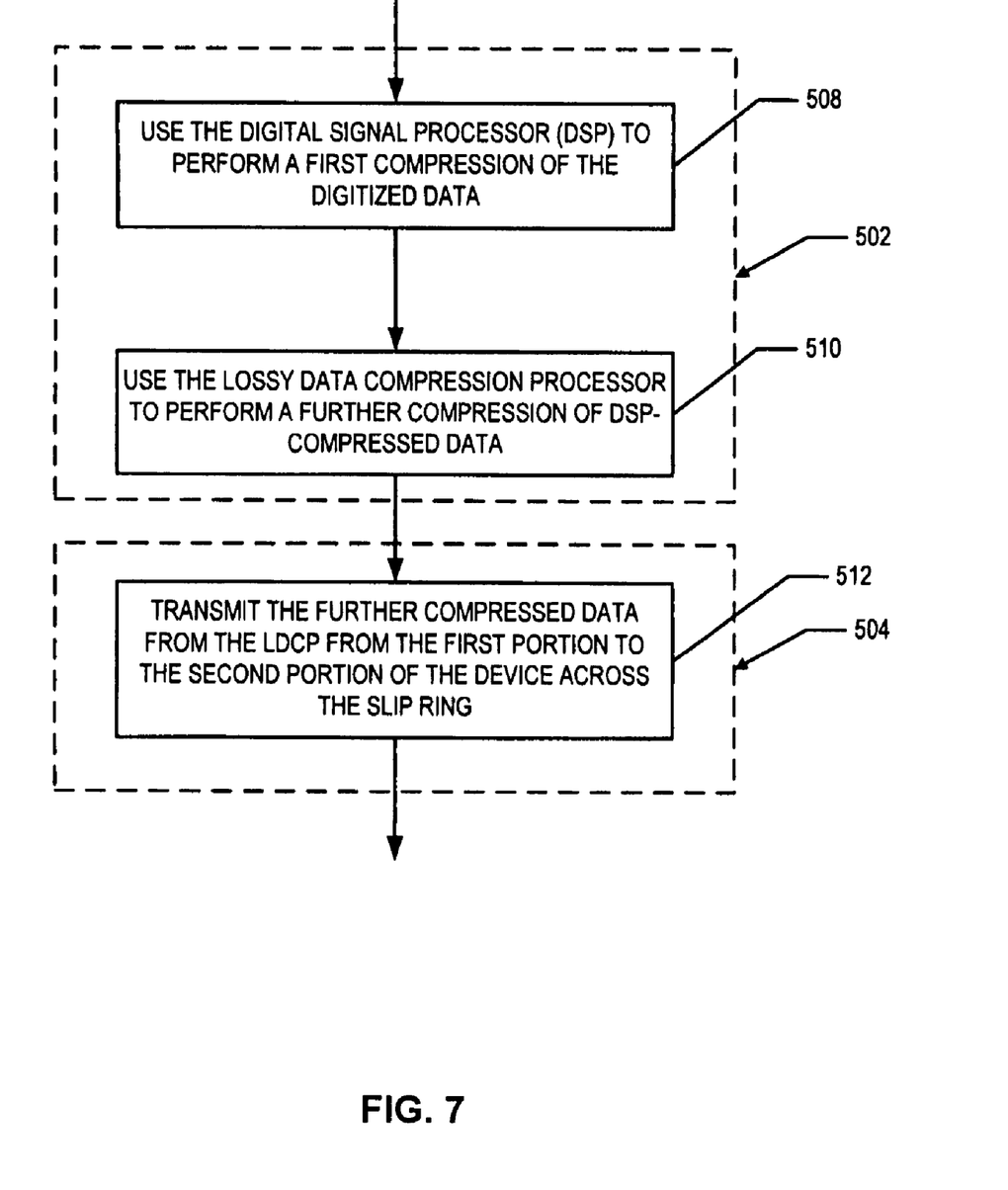
FIG. 7 is a flow chart illustrating further details of portions of the method illustrated in the flow chart of FIG. 6.

FIG. 7 is a flow chart representing further refinements of portions of the method illustrated in flow chart 500 of FIG. 6. More particularly, in some embodiments of the present invention, using DAS 42 to compress data at 502 further comprises, at 508, using DSP 210 to perform a first compression of the digitized data, and, at 510, using LDCP 220 to perform a further compression of the DSP-compressed data. Also, transmitting the compressed data from the first portion to the second portion at 504 further comprises transmitting the further compressed data from LDCP 220 at 510 across slip ring 38.

Figure 8:
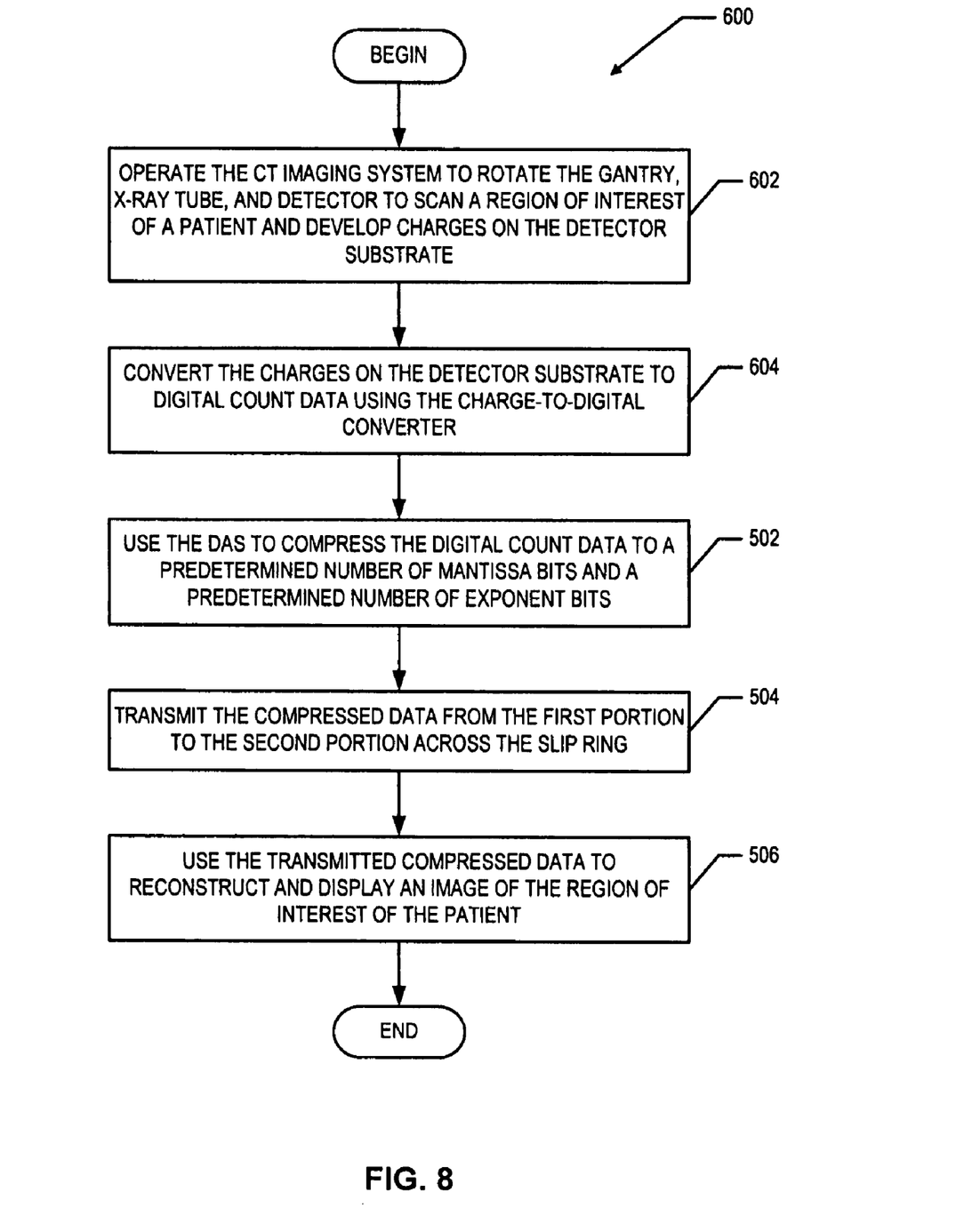
FIG. 8 is a flow chart of a method according to an embodiment of the present invention using a CT imaging apparatus of the type shown in FIGS. 1 and 2.

FIG. 8 is a flow chart 600 of a method of an embodiment of the present invention that can be implemented in the apparatus 10 having the slip ring 38 and wherein the apparatus 10 is a CT imaging apparatus. At 602, CT imaging system 10 is operated to rotate gantry 12, x-ray tube 14, and detector 16 to scan a region of interest of a patient 18 and to develop charges on detector substrate 332. At 604; the charges on detector substrate 332 are converted to digital count scan data using the charge-to-digital converter in ASIC 200. DAS 42 is then used at 502 to compress the digital count scan data to a predetermined number of mantissa, bits and a predetermined number of exponent bits. At 504, the compressed data from 502 is transmitted from apparatus first portion 80 to apparatus second portion 90 across slip ring 38. Next, at 506, computer 24 uses the transmitted compressed data to reconstruct and display an image of the region of interest of patient 18.

In some embodiments of the present invention, the compression at 502 is dependent upon one or more CT scan parameters, a non-exhaustive list of which includes trigger rate, rotation speed, tube kV, tube mA, and scout imaging. The scan parameters are used to optimize or at least improve packing of scan data to be transmitted across the revolving gantry 12. The use of these parameters provides additional information that is used to minimize or at least reduce the number of bits needed for the representation of the transmitted data. The kV and/or mA of x-ray tube 14 and/or the trigger rate of DAS 42 are used to estimate the maximum dynamic range of a scan. From this maximum dynamic range, a minimum number of bits necessary for transferring scan data across the rotating gantry via slip ring 38 is determined. The result in some embodiments is a fixed compression ratio, while in others, a view dependant dynamically changing data compression (between 6 and 16 bits) is determined.

Some embodiments of the present invention use derived scan properties from a scout image to determine the actual dynamic range of a scan, and to aid in the identification and grouping of channels having similar magnitudes at 502. These channels are more correlated, and thus can be compressed more efficiently. By using a scout image to identify channels that have correlated signals in advance, the expected correlation can then be used to more efficiently compress scan data on the first portion 80, i.e., the rotating side of the gantry (for example, by transmitting ratios of data or differences in data across the rotating gantry rather than raw scan data).

From the scout image, the area and/or density of a patient are determined and a measure of the roundness and/or uniformity of the patient are determined, thus permitting dynamic range to be estimated on a view-by-view basis. Thus, a reduction in the number of bits needed to represent scan data can be achieved. The area and/or density and roundness and/or uniformity are already determined for other reasons in some previously known CT imaging systems, however, this formation is not known to be used for accurately determining the dynamic range of the patient depending on what area is being scanned. In some embodiments, the channels that are expected to have similar magnitudes in the data are grouped and identified to increase correlation between channels and thereby reduce the number of bits needed to represent scan data. Some embodiments determine whether or not the difference between highly correlated channels is much smaller than the actual magnitude of the channels. In this case, a significant reduction in data transferred across the slip ring can be achieved. Alternatively, some embodiments can transmit the ratios of data from channels to reduce the amount of bits needed for encoding the result, when appropriate.

The above methods do not necessarily result in a fixed data compression ratio on a scan-to-scan basis, but do allow for significantly less data to be stored (and thereby effecting a reduction in required disk space) without compromising image quality.

In another embodiment, compression at 502 depends only on the trigger rate of DAS 42, resulting in a fixed data compression rate as a function of trigger rate. No further loss in information need occur in this embodiment. Linearity is conserved and the compression conserves the proper number of quantum noise bits in order to keep I/Q data signals uncompromised.

The trigger rate multiplied by the number of bits used is directly related to the transfer data rate. As a result, in at least some previously known CT imaging apparatus 10 embodiments, the fastest trigger rate dominates the transfer rate of slip ring 38. However, by reducing the number of bits needed at the fastest trigger rates, it is possible to reduce the data transfer rate. Table I below shows the data rate reduction as a function of trigger rate in one embodiment.

TABLE I

Data rate reduction as a function of trigger rate

| Trigger Rate (Hz) | Current # of Bits | Compressed # of Bits | Data Rate Reduction |
|---|---|---|---|
| 984 | 16 | 16 | 0% |
| 3500 | 16 | 15 | 6.25% |
| 7320 | 16 | 14 | 12.5% |

In some embodiments of the present invention, compression at 502 is achieved in apparatus 10 by moving functionality to the rotating side of the CT gantry slip ring 38. By moving functionality to the rotating side, a more highly correlated data set can be generated than is generated if the functionality were to remain on the stationary side. This more highly correlated data set can be compressed more than a less correlated data set.

For example, in one embodiment, view compression, offset correction, and reference normalization are brought to the rotating side without interfering or changing the image reconstruction flow. Performing offset correction and then compressing the scan data can result in a loss of resolution and can compromise I/Q data beyond that which is acceptable for some imaging uses. However, in one embodiment of the present invention, the entire offset correction operation followed by reference normalization is performed on the rotating side, followed by transfer of the normalized data to the stationary side where image reconstruction then occurs. Combining the entire offset correction with the reference normalization on the rotating side introduces a higher correlation in the data set than can be achieved if these operations were performed on opposite sides of the rotating gantry.

By moving additional data conditioning functions (e.g., functions that have been performed in known CT imaging systems on the stationary side) to the rotating side, a more highly correlated data set can be obtained. Normalization and air calibration removes variations due to manufacturing. Relatively highly correlated data sets are obtained that can be compressed to a relatively small dynamic range, because correlated data is easier to compress, regardless of the compression scheme used in any particular embodiment. For example, ratios and differences can be transmitted across the slip ring instead of absolute magnitudes for all channels, thereby inherently providing less data to encode.

Furthermore, some embodiments of the present invention perform angular calibration and air calibration on the rotating side of the gantry to introduce even further increased correlation between data samples for compression at 502. The purpose of the angular calibration and the air calibration is to normalize gain differences between detector channels and to work with differences between signals in the calibrated channels. If all channels were excited by the same signal, ideally, each channel would have an identical output. However, prior to air calibration, this ideal output is not achieved because each channel is subject to gain variations that result from manufacturing processes and tolerances. The calibrated dataset does not suffer from such gain variations and can be compressed more efficiently. In imaging systems that perform 3D-scatter correction in image reconstruction between the steps of reference normalization and angular calibration, 3-D scatter correction is moved to the rotating side. Alternately, a 3-D scatter algorithm can be used that acts on air calibrated data on the stationary side of the rotating gantry.

Some embodiments of the present invention provide compression that is dependent upon CT scanner geometrical sensitivity. A lossy compression scheme is optimized or at least improved by using linearity relief inherently provided by the geometry of a CT imaging system for channels having increasing distance from the iso-center of the imaging system. Preferential treatment is applied for image data at the center of the detector of the CT imaging system, whereas a reduced amount of data is transferred for image data in regions of the detector where physical effects mask the degradation that would otherwise occur. The number of bits that are required to preserve clinically useful information at increasing distances from the center of the detector is reduced in accordance with the distance from the center of the detector and determined tradeoffs between dynamic range, linearity and quantum noise.

In one embodiment of the present invention, the linearity requirement is relaxed at distances further from the center of the detector. Thus, the number of bits that must be sent to preserve the required degree of linearity decreases, allowing compression that results in a reduction in the data transfer rate required across the slip ring.

It is important to note that linearity and quantum noise are both important factors in achieving satisfactory image quality. There is a fundamental limit to how much linearity or quantum noise resolution can be degraded individually or in concert before one or both of the factors predominate in a reconstructed image, resulting in degraded quality. By balancing the linearity performance degradation with the quantum noise limitations, data compression can be optimized or at least improved.

Some embodiments of the present invention perform spatial compression of CT channel data in the x- and z-coordinate directions. CT imaging resolution drops off in channels as the distance of the channel from the iso-center increases. The need for precision detection cells thus is limited by the resolution of the CT imaging system at channels far from the iso-center rather than by the physical cell size of a detector channel. Thus, prior to transmission of the data across the slip ring 38, some embodiments of the present invention compress data from a channel as a function of distance of the channel from the iso-center. These embodiments compress acquired data to a greater degree (e.g., more loss is acceptable) in channels farther away from the iso-center than in channels closer to the iso-center. An analysis of the performance requirements (linearity and noise) of each channel in the system is performed, and next, a hybrid floating point compression (described below) is adjusted in to reduce or minimize the acquired data that must be transmitted across the slip ring 38. These embodiments of the present invention reduce the total number of bits required to produce a good image, as channels away from iso-center are combined and therefore less data need be transmitted across the slip ring 38. In addition, some embodiments of the present invention combine other data on the rotating side of the slip ring 38 by taking an average as determined by analysis of optimal cell combinations. Such embodiments require less information to achieve an image of essentially equal quality to that of embodiments that do not combine this other data. The result is effectively equal to a lossy compression, although the loss is quite small.

A hybrid floating point compression method embodiment suitable for embodiments described immediately above compresses DAS system data into a lossy format and ships the data across slip ring 38. The hybrid floating point compression conserves and/or minimizes data transmission bandwidth and/or reduces costs of slip ring 38 and supporting stationary side hardware. To avoid problems with noise normality (and effects of quantization on the image quality), system linearity, and signal dynamic range, the number of floating point mantissa bits and the partitioning of the floating point exponent is carefully chosen, dependent on a plurality of system parameters that may including trigger rate, tube kV, tube mA, the gain of the detector (optical and geometric), the light output of the scintillator, the electronic noise floor of the DAS, the resolution of the DAS, the step size of the DAS (LSB), and the LSB of the system.

At least one hybrid floating point compression method embodiment uses static parameters (that are customized per imaging system), including the gain of the detector (optical and geometric), the light output of the scintillator, the electronic noise floor of the DAS, and the resolution of the DAS. The method also uses dynamic parameters (that change within a system), including trigger rate, X-ray tube kV, X-ray tube mA, the step size of the DAS (LSB), and the LSB of the imaging system.

A hybrid floating point compression method embodiment can be utilized in any ct system through the characterization of the linearity degradation, determination of the noise bit requirements, and determination of dynamic range. A preferred partition of mantissa and exponent as well as exponent ranges can be determined by attempting to optimize both linearity and noise requirements within a required dynamic range.

Prior to compression, data is digitally scaled to dynamically change with rotation speed and trigger rate to maximize performance and minimize loss.

Some hybrid floating point method embodiment carry multiple hidden and encoded MSBs (most significant bits) to optimize or at least increase bit utilization and minimize or at least decrease the total number of bits.

At least one suitable hybrid floating point method embodiment is based on particular CT systems components, including dynamic range of the DAS, kV and mA of the x-ray tube, detector gain (optical and geometric), the light output of the scintillator, the electronic noise floor of the DAS, the resolution of the DAS, the step size of the DAS (LSB), and the LSB of the system.

Data from the DAS is pre-scaled before compression. This pre-scaling is dependent upon linearity requirements, dynamic range and quantum noise resolution requirements. Pre-scaling can also be used to maximize or at least increase the resolution (for a given number of data transmission bits) for a given range of signals dependant on the required LSB for the imaging system, the LSB of the DAS, and their associated performance specifications.

A range of values to encode is determined in accordance with the dynamic range of the imaging system. This dynamic range is dependent upon parameters such as x-ray tube kV, x-ray tube mA, the detector optical gain, the detector geometric efficiency, and scintillator light output. The dynamic range can also be affected by the pre-scaling described above. The maximum number to encode is $2^{max\_DR}$, where max_DR is the number of bits that represent the dynamic range.

max_DR itself can be broken down into a mantissa and an exponent: $(2^{mantissa\_bits}-1) \times 2^{max\_real\_exponent}$. The resolution required (i.e., the effective number of mantissa bits required) is determined in some embodiments by balancing linearity requirements and quantum noise resolution requirements for the imaging system, in accordance with a required imaging system performance and a required image quality. Once the effective number of mantissa bits is determined, the encoding begins with a real exponent of 0, and ends with the value max_real_exponent.

To determine the number of exponent bits, the number of exponent values needed is counted consecutively to reach a value that covers the total dynamic range. For example, if 14 effective bits and a dynamic range of 23 bits are needed, then the total number of consecutive exponents needed is 10 (namely, 0 through 9). In at least one embodiment, consecutive exponent values are maintained to maximize resolution and to allow for the eventual maximum number of encodable hidden MSB bits.

In embodiments in which an excess of exponent values exists (for example, 4 exponent bits are needed, but only 10 actual consecutive values of exponents are needed, 6 excess exponent values are available), the excess exponent values can be used for the encoding of additional hidden MSB bits. For example, encoding of additional hidden MSB bits can be done by reusing a lower exponent value to cover the range of the next highest exponent, thereby increasing the resolution and hiding an extra MSB. Additional encoding to hide more bits can be done by using numerical properties of the exponent range (for example, taking advantage of the evenness or oddness and the reoccurrence of patterns in the hidden MSB bits).

For example, let us consider an embodiment in which the dynamic range is 23 bits, and the effective resolution required is 14 bits. Thus, max_real_exponent is 9, and 10 exponent values or 4 bits are required. Because 4 bits are required for max_real_exponent equal to 9, several excess exponent values remain to carry encoded hidden MSB information. Thus, the full dynamic range can be covered while encoding 2 bits of hidden MSB data, so that 14 bits of effective resolution is achievable with 12 bits of mantissa and 4 bits of exponent. In fact, this encoding is superior to an encoding with 14 mantissa and 2 exponent bits (given the same dynamic range) because using 12 bits of mantissa with 4 bits of exponent allows for the prolonged use of lower values exponents to cover the same range of numbers with less truncation of the covered numbers. The subset of codes which are extended is a function of the system's quantum noise requirements and linearity requirements.

Thus, some embodiments of the present invention hide a plurality of MSBs as encoded parts of the exponent, as opposed to at least one known standard floating point encoding method which hides only a single MSB.

For decoding, some embodiments of the present invention utilize the relationships:

1) New Mantissa=Hidden MSBs followed by Mantissa
2) Value=New Mantissa$\times 2^{(decoded\ real\ Exponent)}$ The encoding method is slightly different than the decoding method in some embodiments to effectively implement a rounding operation rather than a truncation operation. As a result, all exponent ranges require an addition of an LSB/2 prior to encoding in order to effectively become rounded. Thus, values get an LSB/2 added to them prior to the bit truncation operation, which is the final encoding step.

The effective rounding operation reduces the structured error in the number system. The error transforms to within +/− LSB/2 instead of 0 to LSB for any given number, making the structured error better resemble noise, and reducing the error in linearity caused by the process, thereby improving the quality of the image once reconstructed.

It will be understood that the number of exponent bits in an embodiment can be zero, and that a function can be used to make the data an encoded value having only a mantissa. Such functions can be simple functions such as logo or more complicated functions such as a piecewise function. In the latter case, the number of additional bits (exponent bits) may grow.

One embodiment of the present invention compresses data by combining channel data from channels distant from the iso-center. For example, at least one known prior art CT imaging system transmits 912 channels of data from the DAS across the slip ring. However, in an embodiment of the present invention, channel data in a 912 channel imaging system is combined in the manner specified in Table II below.

TABLE II

Combination of channels according to distance from iso-center

| Channel | Compression | Reason | Reduction |
|---|---|---|---|
| 1-2 | 2:0 in X | Unused for reconstruction | 2 channels |
| 3-8 | 6:1 in X | End use is Averaging | 5 channels |
| 9-128 | 2:1 in X | System resolution Drop-off | 60 channels |
| 129-768 | 1:1 in X | Resolution Requirement | 0 channels |
| 769-860 | 2:1 in X | System resolution Drop-off | 46 channels |
| 861-896 | 3:1 in X | System resolution Drop-off | 24 channels |
| 897-908 | 4:1 in Z | Tracking Limited | 9 channels |
| 909-912 | 3:0 in X | Unused for reconstruction | 3 channels |

The embodiment described above provides a fixed data bandwidth reduction (corresponding to an equivalent data transmission rate reduction) of more than 16%. This reduction is accomplished through compression and software, whereas at least one known prior art CT imaging system reduced bandwidth transmission across the slip ring using various types of hardware (e.g., diodes and FETs). The reduction gained by embodiments of the present invention thus is achieved at a reduced cost.

In some other embodiments of the present invention, the software on the rotating side of the gantry and the stationary side of the gantry are configured so that calibration vectors (including, for example, offset, angular calibration, and air calibration, etc.) can be collected for individual pixels and then transmitted across the slip ring as 912 channels for host processing, or can be compressed on the rotating side and transmitted in compressed form for reduced bandwidth. Further reductions in data can be achieved in other embodiments by not transmitting tracking data (which is possible because tracking data feedback can be contained completely on the rotating side).

Some embodiments of the present invention perform compression using a temporal correlation of samples. Samples from a CT imaging system that triggers quickly or that uses focal spot deflection (or wobble) are much more highly correlated than neither, so embodiments of the present invention provide greater data bandwidth across the slip ring than known prior art CT imaging systems.

In an experiment, different types of compression methods using temporal correlation were tested. Without compromise to image quality, an additional fixed compression rate of 12.5% was achieved using real data with three-point focal spot deflection, and an additional fixed compression rate of about 10% was achieved with two-point focal spot deflection. These compression methods were tested using five different phantoms that were selected to stress the CT imaging system.

As the sampling rate of a channel increases, temporal correlation of samples within that channel increases. Thus, a high correlation between samples can be expected if the sampling rate is increased sufficiently. Focal spot deflection (a.k.a. wobble) inherently increases the sampling resolution, thereby increasing temporal correlation. Any temporal compression method can be tried to determine empirically whether the method can successfully reduce the required transmission bandwidth. At least four methods that can be used for compression each keep one of the wobble views intact and encode the temporally correlated samples with fewer bits than a base view. These methods are:

(1) A difference method, which eliminates two exponent bits, and adds a sign bit. The exponent bits are eliminated by first encoding the difference in the mantissa bits of the samples and with a sign bit and the original exponent of the base number.

(2) A raw ratio method in which a ratio of the full view and the base view is first determined. Two exponent bits are then removed. This method uses a number less than one, so an inversion bit is added to keep track of whether the value is to be inverted or not. The ratio is then encoded and multiplied by a pre-determined scale factor after transmission across the slip ring.

(3) A ratio method that is essentially the same as the raw ratio method, except that after conversion, the ratio result is converted into a compressed floating point space value.

(4) A modified ratio method. This method is also essentially the same as the raw ratio method, except that after conversion, the result is converted back into a modified floating point space value. More particularly, there is no pre-rounding, but the result is rounded instead of floored.

It will thus be appreciated that methods and apparatus of the present invention provide a bandwidth reduction of communication across a slip ring between two portions of an apparatus rotating with respect to one another. In the case of a CT imaging system, the reduced bandwidth can be used to produce image scans having greater speed and/or more slices that is possible without such bandwidth reduction and/or reduce the cost of existing slipring and data storage hardware.

At least one technical effect of the various embodiments of the invention is to provide a bandwidth reduction of communication across a slip ring between two portions of an apparatus rotating with respect to one another. In the case of a CT imaging system, the reduced bandwidth can be used to produce image scans having greater speed and/or more slices than is possible without such bandwidth reduction and/or potentially reduce the cost of existing slipring and data storage hardware.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method for compressing data for transmission via a slip ring connector in a medical imaging system, the method comprising:
    configuring a slip ring connector to transmit data from a data acquisition system (DAS) to a computer of the medical imaging system;

configuring the DAS to acquire raw data in a plurality of channels and compress the acquired raw data using data compression based on a scout image that provides a measured dynamic range of data to identify a plurality of channels with similar data magnitudes, for transmitting from the DAS to the computer via the slip ring connector; and configuring the computer to reconstruct at least one image using the compressed data.

2. The method of claim 1, wherein the DAS performs an initial compression of the acquired raw data prior to data compressing the raw data.

3. The method of claim 2, wherein the initial compression is performed using a floating-point compression method.

4. The method of claim 1, wherein a compression ratio of the acquired raw data, in each of the plurality of channels, is provided using at least one of a fixed compression ratio or a dynamic compression ratio.

5. The method of claim 1, wherein the data compression, from the plurality of channels, comprises identifying the plurality of data channels having correlated signals, and compressing the data using the identified correlation.

6. The method of claim 1, wherein the data compression is also performed using the functionality of the DAS comprising a rotation function of a gantry.

7. The method of claim 1, wherein the data compression is also performed using the functionality of the DAS comprising performing at least one of an offset correction, a view compression, a reference normalization, or a three-dimensional scatter correction.

8. The method of claim 1, wherein the data compression is performed by also using the functionality of the DAS comprising at least one of a calibration for angular deviation or an air calibration.

9. The method of claim 1, wherein the data compression is performed by also using the geometric sensitivity of the DAS comprising at least one of a linearity of data, a dynamic range of data, or a quantum noise of data in detectors positioned relative to an iso-center of the medical imaging system.

10. The method of claim 1, wherein the data compression is performed by also using the two dimensional spatial compression comprising at least one of an image quality, or a data resolution relative to an iso-center of the medical imaging system.

11. The method of claim 1, wherein the data compression is performed by also using the two dimensional spatial compression comprising compression using only software.

12. The method of claim 1, wherein the data compression is performed by also using the temporal correlation of data comprising a focal spot deflection of the DAS.

13. The method of claim 1, wherein the configuring the DAS further comprises configuring the DAS to compress the acquired raw data using data compression based also on image scanning parameters.

14. A medical imaging system comprising:
a data acquisition system (DAS); and
a computer connected to the DAS via a slip ring connector, the slip ring connector configured to transmit data from the DAS to the computer,
wherein the DAS is configured to acquire raw data in a plurality of channels and compress the acquired raw data using a scout image that provides a measured dynamic range of data to identify a plurality of channels with similar data magnitudes, and the computer is configured to reconstruct at least one image using the compressed data.

15. The medical imaging system of claim 14, wherein the acquired raw data is initially compressed prior to the data compression.

16. The medical imaging system of claim 15, wherein the initial compression is a floating-point compression.

17. The medical imaging system of claim 14, wherein a compression ratio of the acquired raw data is at least one of a fixed compression ratio or a dynamic compression ratio.

18. The medical imaging system of claim 14, wherein during the compression of data, from the plurality of channels, the DAS is configured to identify the plurality of data channels having correlated signals, and compress the data using the identified correlation.

19. The medical imaging system of claim 14 further comprising a computed tomography imaging gantry having an x-ray tube and detector array.

20. The medical imaging system of claim 14, wherein the data compression is also based on image scanning parameters.

* * * * *